US00PP27095P2

(12) United States Plant Patent
Hartman

(10) Patent No.: US PP27,095 P2
(45) Date of Patent: Aug. 23, 2016

(54) ***CALADIUM* PLANT NAMED 'RADIANCE'**

(50) Latin Name: *Caladium×hortulanum*
Varietal Denomination: Radiance

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 88 days.

(21) Appl. No.: 14/544,172

(22) Filed: Dec. 4, 2014

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Radiance', characterized by its compact, upright and uniformly mounded plant habit; vigorous growth habit and very rapid growth rate; fancy-type leaves that are bright pink in color with dark pink-colored centers, red-colored venation and dark green-colored margins; and good landscape performance.

4 Drawing Sheets

Botanical designation: *Caladium×hortulanum.*
Cultivar denomination: 'RADIANCE'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Radiance'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2007 in Avon Park, Fla. of *Caladium×hortulanum* 'Red Flash', not patented, as the female, or seed, parent with a proprietary selection of *Caladium×hortulanum* identified as code number WS-03-36, not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2008.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since March, 2009 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Radiance'. These characteristics in combination distinguish 'Radiance' as a new and distinct *Caladium* plant:

1. Compact, upright and uniformly mounded plant habit.
2. Vigorous growth habit and very rapid growth rate.
3. Fancy-type leaves that are bright pink in color with dark pink-colored centers, red-colored venation and dark green-colored margins.
4. Good landscape performance.

Plants of the new *Caladium* differ primarily from plants of the female parent, 'Red Flash', in the following characteristics:

1. Plants of the new *Caladium* are more compact and mounding than plants of 'Red Flash'.
2. Plants of the new *Caladium* are faster growing and produce finished plants about two to three weeks earlier than plants of 'Red Flash'.
3. Plants of the new *Caladium* and 'Red Flash' differ in leaf color as leaves of plants of 'Red Flash' are dark green in color with dark red-colored centers and primary veins and pink-colored spots.

Plants of the new *Caladium* differ primarily from plants of the male parent selection in the following characteristics:

1. Plants of the new *Caladium* are faster growing and produce finished plants about one week earlier than plants of the male parent selection.
2. Plants of the new *Caladium* and the male parent selection differ in leaf shape and color as leaves of plants of the male patent selection are lance leaf-types that are dark green in color with grey green-colored centers occasionally blushed with pink.

Plants of the new *Caladium* can be compared to plants of *Caladium×hortulanum* 'Mrs. Arno Nehrling', not patented. In side-by-side comparisons, plants of the new *Caladium* differed primarily from plants of 'Mrs. Arno Nehrling' in the following characteristics:

1. Plants of the new *Caladium* were more compact and uniformly mounding than plants of 'Mrs. Arno Nehrling'.
2. Plants of the new *Caladium* were faster growing and produced finished plants about one week earlier than plants of 'Mrs. Arno Nehrling'.
3. Plants of the new *Caladium* and 'Mrs. Arno Nehrling' differed in leaf color as leaves of plants of 'Mrs. Arno Nehrling' were green in color with white to tan pink-colored interveinal areas and red-colored venation.

Plants of the new *Caladium* can also be compared to plants of *Caladium×hortulanum* 'White Queen', not patented. In side-by-side comparisons, plants of the new *Caladium* differed primarily from plants of 'White Queen' in the following characteristics:

1. Plants of the new *Caladium* were more compact and uniformly mounding than plants of 'White Queen'.
2. Plants of the new *Caladium* were faster growing and produced finished plants about one week earlier than plants of 'White Queen'.
3. Plants of the new *Caladium* and 'White Queen' differed in leaf color as leaves of plants of 'White Queen' had white to pink-colored interveinal areas with red-colored venation surrounded by red pink-colored areas.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Radiance' in a container and grown in a shadehouse (tuber not de-eyed).

The photograph at the top of the second sheet is a comparison view of typical potted plants of the female parent, 'Red Flash' (left), 'Radiance' (center) and the male parent selection (right).

The photograph at the bottom of the second sheet is a comparison view of typical potted plants of 'White Queen' (left), 'Radiance' (center) and 'Mrs. Arno Nehrling' (right).

The photograph at the top of the third sheet is a side perspective view of typical plants of 'Radiance' grown in an open field.

The photograph at the bottom of the third sheet is a comparison view of typical plants of 'Radiance' grown in containers; the plant on the left has not had its tuber de-eyed and the plant on the right has had its tuber de-eyed prior to planting.

The photograph at the top of the fourth sheet is a close-up view of typical freshly-harvested tubers and roots of 'Radiance'.

The photograph at the bottom of the fourth sheet is a close-up view of a typical inflorescence of 'Radiance'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were four weeks old, and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Radiance'.

Parentage:

*Female, or seed, parent.*—*Caladium×hortulanum* 'Red Flash', not patented.

*Male, or pollen, parent.*—Proprietary selection of *Caladium×hortulanum* identified as code number WS-03-36, not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and somewhat flattened; individual segments elliptic or irregular. Height: About 3.5 cm. Diameter: About 4.6 cm to 5.1 cm. Segment height: About 1.5 cm to 2 cm. Segment diameter: About 1.3 cm to 1.8 cm. Texture: Thick, starchy; somewhat brittle. Color: Epidermis, freshly-harvested: Close to 199A to 199B. Epidermis, dried: Close to 200A. Cortical tissue: Close to 2D. Axillary buds: Close to N170D and 36D. Root description: Thick, fleshy contractile roots; color, close to 155C and 199C. Rooting habit: Medium density.

Plant description:

*Plant type.*—Herbaceous perennial; suitable as a potted plant in containers 15-cm to 25-cm and suitable as a landscape plant in shaded areas.

*Plant and growth habit.*—Compact, upright and uniformly mounded plant habit; vigorous and dense growth habit; very rapid growth rate, potted plants in finished or saleable form in about four weeks after planting tubers; leaf petioles and leaves arise from one or more growing points on tubers; petioles mostly upright and leaning outwardly with development.

*Plant height, from soil level to top of foliar plane, shadehouse-grown potted plants.*—About 24 cm to 28 cm.

*Plant height, from soil level to top of inflorescences, shadehouse-grown potted plants.*—About 28 cm.

*Plant diameter or spread, shadehouse-grown potted plants.*—About 30 cm to 34 cm.

*Number of shoots per plant, shadehouse-grown potted plants, tubers not de-eyed.*—About one to two develop per #1 tuber.

*Number of shoots per plant, shadehouse-grown potted plants, tubers de-eyed.*—About two to three develop per #1 tuber.

*Cataphylls, shadehouse-grown potted plants*.—Length: About 6 cm to 7.9 cm. Width: About 1 cm to 1.3 cm. Shape: Ligulate to somewhat wedge-shaped. Apex: Acuminate to cuspidate. Base: Sheathing the stem. Color, inner surface: Close to N155C; colors and patterns of the outside surface are visible on the inner surface. Color, outer surface: Close to 177D and N170D and stippled, streaked and tessellated with close to 147A tinged with close to N199A; with development, color becoming closer to 199B to 199C and N199B.

Leaf description:

*Arrangement and type*.—Alternate; simple; fancy-type.

*Length, shadehouse-grown potted plants*.—About 16.5 cm to 22 cm.

*Width, shadehouse-grown potted plants, flattened*.—About 11.2 cm to 14 cm.

*Shape*.—Broadly ovate.

*Apex*.—Acute.

*Base*.—Sagittate to peltate.

*Margin*.—Entire; mostly flat with broad undulations.

*Texture, upper and lower surfaces*.—Smooth, glabrous.

*Luster, upper surface*.—Dull sheen.

*Luster, lower surface*.—Glaucous, dull sheen.

*Venation pattern*.—Pinnate.

*Color, shadehouse-grown potted plants*.—Developing leaves, upper surface: Interveinal colors: Random areas of close to 147A to 147B, 146B, 48C and 48D; towards the margins, close to 147A flecked with close to 49D. Margin edge: Close to 187B. Basal notch: Close to 187A. Midrib and primary venation: Close to 53A; areas adjacent to venation, close to 53A to 53B. Developing leaves, lower surface: Interveinal colors: Random areas of close to 191B tinged with close to 146B, 49C and 51D; towards the margins, close to 191A and 191B. Margin edge: Close to 187B. Basal notch: Close to 187A. Midrib and primary venation: Close to 182C to 182D; areas adjacent to venation, close to 184B. Fully expanded leaves, upper surface: Interveinal colors: Close to 48B to 48C; towards the margins, close to 147A flecked with close to 48B. Margin edge: Close to 187B. Basal notch: Close to 187A. Midrib and primary venation: Close to 53A; areas adjacent to venation, close to 53B to 53C. Secondary venation: Close to 147A and close to between 147A and 146B. Fully expanded leaves, lower surface: Interveinal colors: Close to 49C and 51C to 51D; towards the margins, close to 191B flecked with close to 49D. Margin edge: Close to 187B. Basal notch: Close to 187A. Midrib and primary venation: Close to 182D; areas adjacent to venation, close to 184B. Secondary venation: Close to 146B.

*Petioles*.—Aspect: Initially upright and straight; with development, leaning outwardly; flexible. Length, shadehouse-grown potted plants: About 23.5 cm to 26.5 cm. Diameter, distal, shadehouse-grown potted plants: About 3.5 mm to 4 mm. Diameter, proximal, shadehouse-grown potted plants: About 5 mm to 7 mm. Texture: Smooth, glabrous; glaucous. Color, shadehouse-grown potted plants, Just below the leaf and petiole junction: Close to 182A and 182C to 182D. Overall: Close to 170D and N170D, stippled, streaked and tessellated with close to 147A tinged with close to N199A. Wing length, shadehouse-grown potted plants: About 4.5 cm to 6.5 cm. Wing diameter, shadehouse-grown potted plants: About 7 mm. Texture, inner and outer surfaces: Smooth, glabrous. Wing color, shadehouse-grown potted plants, inner surface: Close to N155D and N170D. Wing color, shadehouse-grown potted plants, outer surface: Close to 177D, N170D and N155D, stippled, streaked and tessellated with close to 147A tinged with close to N199A.

Inflorescence description: Inflorescences observed on four week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring in central Florida; early flowering habit, flowers develop about four weeks after growth commences; inflorescences last about three days before fading; inflorescences persistent.

*Spathe*.—Length, overall: About 9.4 cm. Length, distal open portion: About 6 cm. Length, proximal closed portion: About 3.4 cm. Width, distal open portion: About 3.4 cm. Width, at constriction: About 1.1 cm. Width, proximal closed portion: About 2.5 cm. Shape: Elliptic to ovate. Apex: Acute. Base: Obtuse. Margin: Entire; slightly reflexed. Texture, front and rear surfaces: Smooth, glabrous. Luster, front surface: Dull sheen. Luster, rear surface: Glaucous. Color, front surface: Distal open portion: Close to N155D and N155C; with development, color becoming closer to 199C to 199D. Proximal closed portion: Close to 194B; towards the base, close to N186D and 187C; color does not change with development. Color, rear surface: Distal open portion: Close to 155B and 155C tinged with close to 145D; color does not change with development. Proximal closed portion: Close to 148B to 148C, streaked with close to 147B to 147C and variably flushed or tinged with close to 182A to 182B and 183D; color does not change with development.

*Spadix*.—Length: About 6.5 cm. Length, male flower zone: About 3.4 cm. Length, sterile zone: About 1.5 cm. Length, female flower zone: About 1.6 cm. Diameter, male flower zone: About 8 mm. Diameter, sterile flower zone: About 5 mm. Diameter, female flower zone: About 1 cm. Shape: Columnar. Apex: Obtuse to bluntly acute. Base: Obtuse. Aspect: Upright. Color, mature, male zone: Close to 13D. Color, mature, sterile zone: Close to 11D. Color, mature, female zone: Close to 20C to 20D and 155C. Male flowers: Quantity per spadix: About 60. Shape: Obovate. Height: About 2 mm. Diameter: About 2 mm. Pollen amount: Moderate. Pollen color: Close to 4C. Female flowers: Quantity per spadix: About 95. Shape: Obovate. Height: About 2 mm. Diameter: About 1 mm. Stigma color: Close to 20C to 20D. Ovary color: Close to 155C.

*Scape*.—Length: About 21.5 cm. Diameter: About 5 mm. Strength: Sturdy; flexible. Aspect: Mostly erect. Texture: Smooth, glabrous; slightly glaucous. Color, just below spathe: Close to 146C and 147B tinged with close to 199C to 199D. Color, overall: Close to 199B to 199C tinged with close to 147A, and faintly streaked, stippled and tessellated with close to 147A tinged with close to 199A.

*Seeds and fruits*.—To date, seed and fruit development have not been observed on plants of the new *Caladium*.

Disease & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Radiance' as illustrated and described.

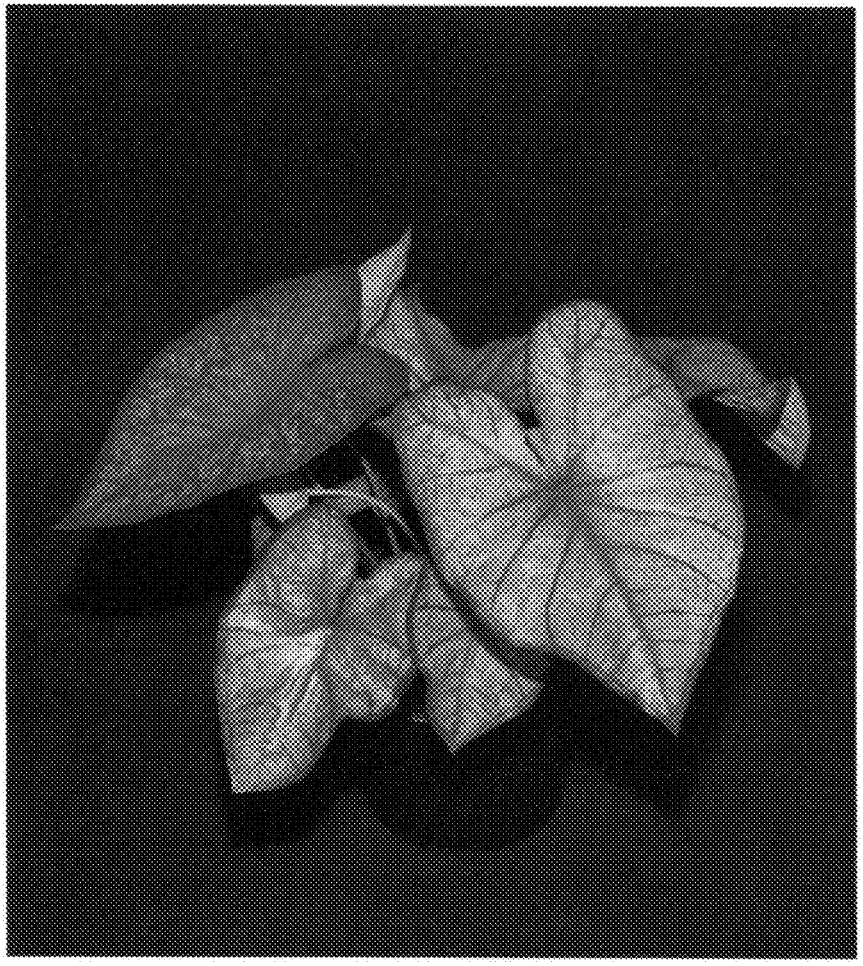

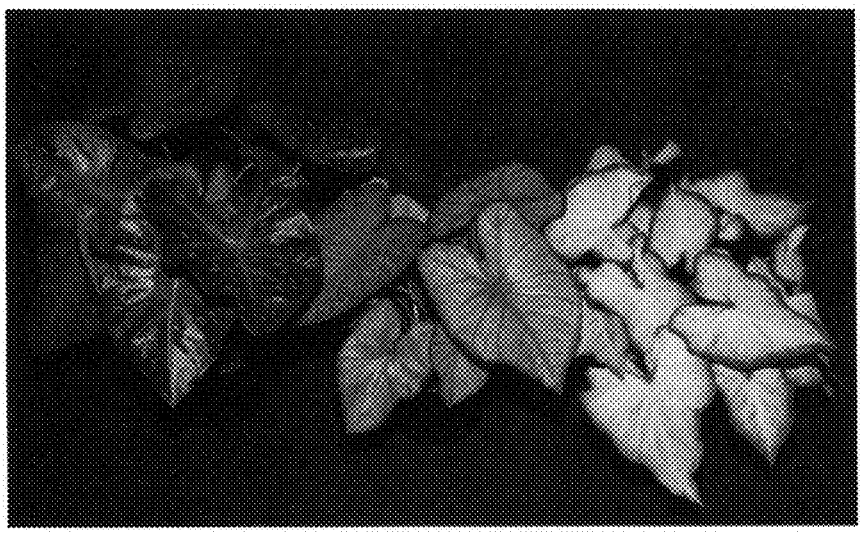
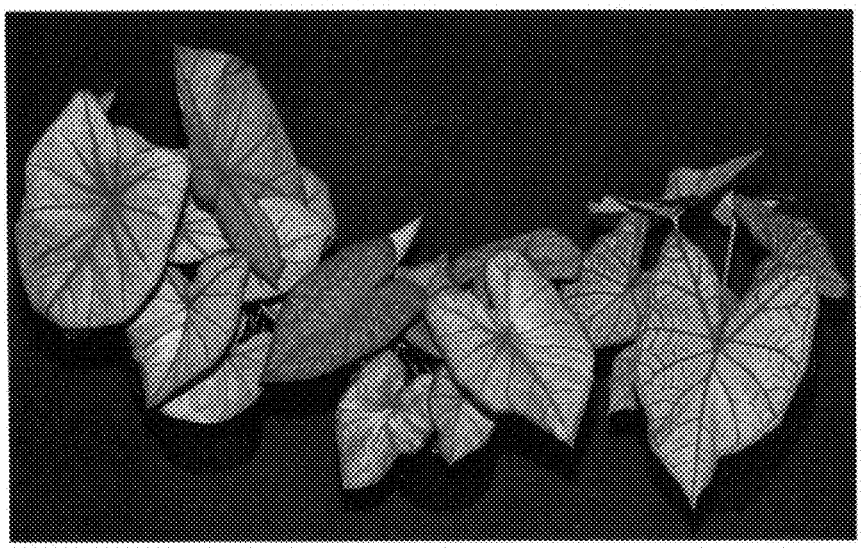

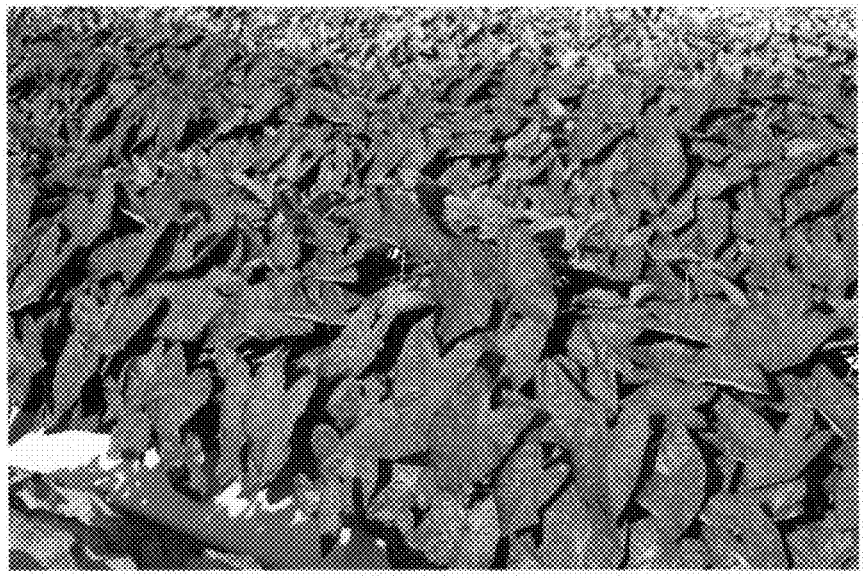
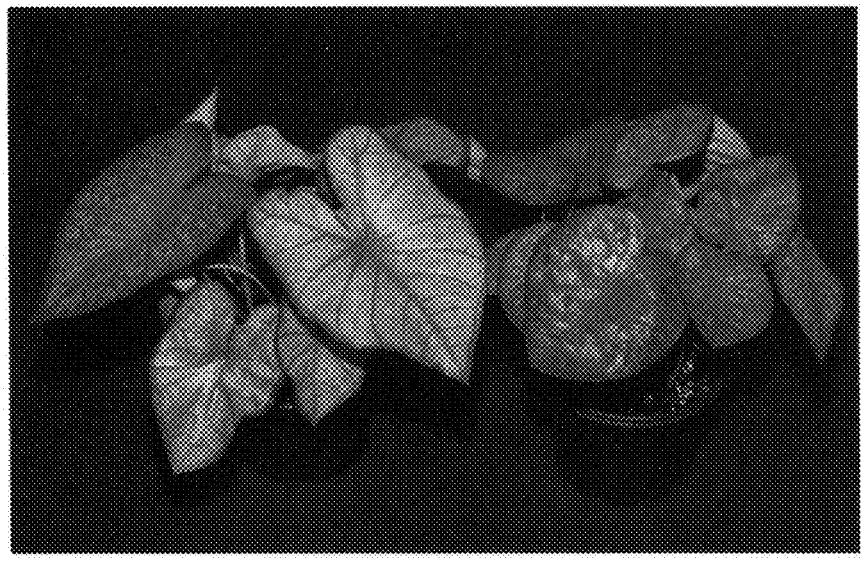

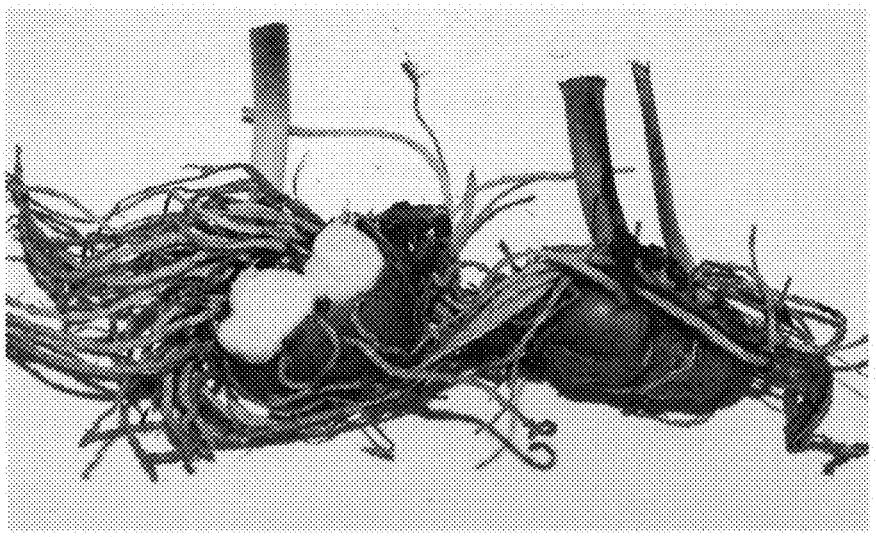
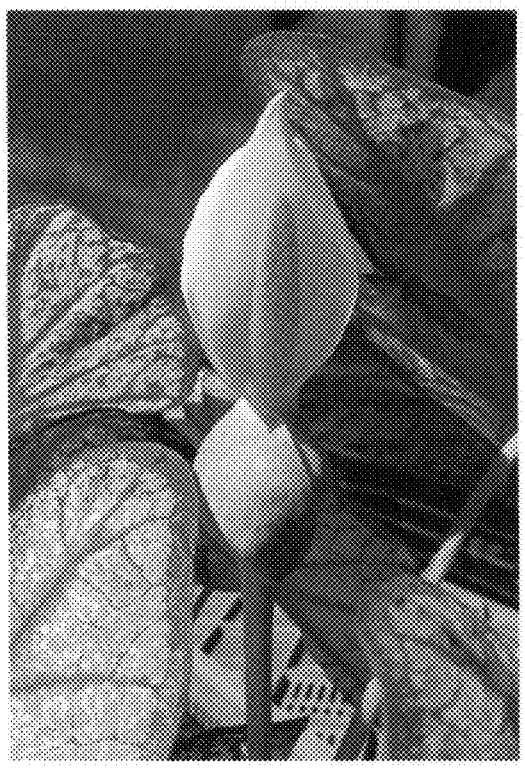

* * * * *